(12) United States Patent
Steenhoek

(10) Patent No.: US 8,374,831 B2
(45) Date of Patent: *Feb. 12, 2013

(54) PROCESS FOR GENERATING BIDIRECTIONAL REFLECTANCE DISTRIBUTION FUNCTIONS OF GONIOAPPARENT MATERIALS WITH LIMITED MEASUREMENT DATA

(75) Inventor: Larry Eugene Steenhoek, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 23 days.

This patent is subject to a terminal disclaimer.

(21) Appl. No.: 13/155,767

(22) Filed: Jun. 8, 2011

(65) Prior Publication Data
US 2011/0234621 A1    Sep. 29, 2011

Related U.S. Application Data

(62) Division of application No. 12/446,993, filed on Apr. 24, 2009, now Pat. No. 7,991,596.

(51) Int. Cl.
*G06F 17/10* (2006.01)
(52) U.S. Cl. ............. 703/2; 382/162; 356/405; 356/907
(58) Field of Classification Search ................... 703/2, 3, 703/5, 6; 708/200; 382/141, 162, 190, 206; 356/402, 405, 907
See application file for complete search history.

(56) References Cited

U.S. PATENT DOCUMENTS

| | | | |
|---|---|---|---|
| 4,479,718 A | 10/1984 | Alman | |
| 6,618,050 B1 | 9/2003 | Rupieper et al. | |
| 6,977,650 B2 | 12/2005 | Voye et al. | |
| 7,639,255 B2 * | 12/2009 | Steenhoek et al. | 345/428 |
| 7,743,055 B2 * | 6/2010 | Rodrigues et al. | 707/722 |
| 7,747,615 B2 * | 6/2010 | Rodrigues et al. | 707/722 |
| 2007/0003691 A1 * | 1/2007 | Rodrigues et al. | 427/140 |
| 2007/0292608 A1 * | 12/2007 | Rodrigues | 427/140 |
| 2009/0019086 A1 * | 1/2009 | Prakash et al. | 707/104.1 |
| 2010/0027870 A1 * | 2/2010 | Rodrigues et al. | 382/141 |

OTHER PUBLICATIONS

Hertzmann et al, "Example-Based Photometric Stereo: Shape Reconstruction with General, Varying BRDF's", IEEE Transactions on Pattern Analysis and Machine Intelligence, vol. 27, No. 8, Aug. 2005, pp. 1254-1264.*
Smith et al, "Skin Reflectance Modeling for Face Recognition", Proceedings of the 17th International Conference on Pattern Recognition, 2004, pp. 210-213.*

(Continued)

*Primary Examiner* — Russell Frejd
(74) *Attorney, Agent, or Firm* — Gann G. Xu

(57) ABSTRACT

A computer-implemented process for generating a bidirectional reflectance distribution function (BRDF) of a gonioapparent material containing effect flake pigments in a solid medium using limited measurement data, comprising the following steps: (A) acquiring and inputting into a computing device (1) photometric data and (2) the refractive index of the solid medium of the gonioapparent material; (B) converting any non-linear photometric data from step A) above to linear photometric data; (C) using the illumination angle and the reflective scattering angle associated with the linear photometric data and the refractive index of the medium to calculate corresponding effect flake angles; (D) fitting the linear photometric data and the effect angle data with an equation; (E) calculating the corresponding effect flake angle needed to calculate the BRDF being generated in step (F); and (F) generating the BRDF from the corresponding effect flake angle from step (E) and the equation developed in step (D).

14 Claims, 6 Drawing Sheets

OTHER PUBLICATIONS

Jafolla et al, "Phenomenological BRDF Modeling for Engineering Applications", SPIE, vol. 3141, 1997, pp. 281-292.*

Raven et al, "Appearance Assessment of Goniochromatic Coatings", OSA/OIC 2001, pp. 1-3.*

Raven et al, "Bidirectional Reflectance from Pigmented Coatings", Part of the SPIE Conference on Scattering and Surface Roughness, vol. 3784, Jul. 1999, pp. 262-273.*

Meyer et al, "A Computer Graphics System for Rendering Gonio-Apparent Colors", Google, iscc.org/aic2001/abstyracts/oral/Meyer_Westlund_Walker.pdf, 2001, pp. 1-4.*

F. E. Nicodemus, J. C. Richmond, J. J. Hsia, I. W. Ginsberg, and T. Limperis, "Geometrical considerations and nomenclature for reflectance," NBS Monograph 160 (National Bureau of Standards, Washington, D.C., 1977).

* cited by examiner

PROCESS FOR GENERATING BIDIRECTIONAL REFLECTANCE DISTRIBUTION FUNCTIONS OF GONIOAPPARENT MATERIALS WITH LIMITED MEASUREMENT DATA

CROSS-REFERENCE TO RELATED APPLICATION

This application is a divisional of U.S. application Ser. No. 12/446,993, filed on Apr. 24, 2009, now U.S. Pat. No. 7,991,596.

FIELD OF THE INVENTION

The present invention relates to a process for the generation of the bidirectional reflectance distribution function (BRDF) of gonioapparent materials or surfaces, specifically those containing effect flake pigments, such as, metallic flake pigments or special effect flake pigments that typically are hue shifting interference pigments, with limited measurement data.

BACKGROUND OF THE INVENTION

One the most general and well accepted means of describing the spectral and spatial reflective scattering properties of a material is by use of the bidirectional reflectance distribution function (BRDF). The BRDF is a fundamental description of the appearance of the surface of a material, and many other appearance attributes (such as, gloss, haze, and color) can be represented in terms of integrals of the BRDF over specific geometries and spectral conditions. Specification of the BRDF is critical to the marketability of consumer products, such as, automobiles, cosmetics and electronics. The microstructure associated with a material affects the BRDF and specific properties can often be inferred from measurement of the BRDF. The angular distribution of reflectively scattered light described by the BRDF can be used to render the appearance of materials or to predict the color appearance under varying geometrical conditions. The quality of the rendering or color prediction depends heavily on the accuracy of the BRDF of the materials being rendered.

Gonioapparent objects or materials exhibit the characteristic of changing their appearance with change in illumination angle or viewing angle. Automotive finishes (paints) containing metallic flake pigments or special effect flake pigments, such as, pearlescent flake pigments are examples of gonioapparent materials. Unlike solid colors which can be characterized at a single measurement geometry, gonioapparent colors require measurements under a variety of illumination and viewing geometries to describe their color appearance characteristics. Finishes containing metallic flakes are generally characterized by making three color measurements at different aspecular angles. ASTM standard E-2194, which is hereby incorporated by reference, describes a standard practice for multi-angle color measurement of metal flake pigmented materials. Finishes containing special effect flake pigments that are hue shifting materials, such as, pearlescent pigments, also must be measured at multiple geometries which vary in both aspecular angle and illumination angle to characterize their color behavior.

In order to render objects on a video screen, or print media, or otherwise predict the color appearance of an object at a given illumination and viewing geometry, the object's color at many thousands of combinations of illumination and viewing angles must be calculated.

There are three basic techniques that have been used for the task of calculating all the required combinations of illumination and view.

1) The first technique is to actually measure the color of the object at several thousand combinations of illumination and view with an instrument such as a goniospectrophotometer, or goniocolorimeter. This requires that a sufficient number of measurements be made so that interpolation of the data to predict the color of the object at intermediate geometries can be done with sufficient accuracy. However, instruments with the required geometric flexibility and photometric accuracy are costly and very slow. Complete characterization of a single color requires several hours of measurement time using this technique.

2) A second technique is to develop a physical model of the finish (color) and then use a technique, such as, radiative transfer theory to calculate the color at all of the required angular combinations. While techniques of this type can be used to produce visually pleasing renderings, development and tuning of the model to match the behavior of a physical standard is extremely difficult and time consuming and may in fact be impossible to do with sufficient fidelity.

3) The third technique is a combination of the first two with the advantage of requiring far fewer measurements than the first technique and a far less rigorous model of the finish than the second technique. This third technique involves making a limited number (typically 3-5) of color measurements of the object to be rendered and then modeling the interpolation of this measured data to the required angular combinations. This technique can utilize 3-angle measurement data already contained in databases typically used to store color characteristics of gonioapparent materials. The models used to extrapolate this data to other angular combinations do not require individual tuning and are based on simple physical parameters of the surface of the material.

For rendering or color prediction applications requiring measurement of a vast array of colors, which match actual physical standards and are not just "realistic looking" synthetic colors, the combination technique as described above is the preferred solution.

Alman (U.S. Pat. No. 4,479,718) led to the eventual wide spread adoption of a three aspecular angle measurement system for characterization of finishes containing metal flake pigments in combination with absorbing and or scattering pigments. This measurement system serves as the basis for such international standards as ASTM E-2194 and DIN 6175-2. In practice, this characterization approach also works well for formulation and control of finishes containing hue shifting (pearlescent) pigments once pigmentation has been established.

While the concept of describing the gonioapparent color behavior of a material by measurements made at three aspecular angles is useful for formulation and control, and can be used to predict if a pair of samples will match under various measurement or viewing geometries, it is not well suited to predict the absolute color of a material as the measurement and viewing geometries change. For instance, while the same general color change predicted by aspecular measurements hold as the illumination angle is changed, the magnitude of the color change is not well predicted. FIG. 2 shows a plot of tristimulus value Y as a function aspecular angle for a variety of illumination angles for an automotive paint specimen containing metal flake pigment. While there is a trend to increasing value of Y as the aspecular angle decreases, there are large differences in the absolute value of Y at a given aspecular angle as the illumination angle is changed.

A method is needed to predict the absolute color of a specimen, under any measurement or viewing geometry, from a limited (<10) set of color measurements.

SUMMARY OF THE INVENTION

The invention is directed to a computer-implemented process for generating a bidirectional reflectance distribution function (BRDF) or variously normalized variants thereof of a gonioapparent material containing effect flake pigments in a solid medium using limited measurement data, comprising the following steps in any appropriate order:

(A) acquiring and inputting into a computing device (1) photometric data comprising spectral or calorimetric data of the gonioapparent material being a function of an illumination angle and a reflective scattering angle, wherein the data is obtained by (a) measurements of the gonioapparent material, (b) previously measured data of the gonioapparent material from a data base containing measurements of the gonioapparent material or (c) simulated data for a gonioapparent material and (2) the refractive index of the solid medium of the gonioapparent material;

(B) converting any non-linear photometric data from step (A) above to a linear photometric data (e.g., converting non-linear colorimetric L*, a*, b* data to linear X, Y, Z data);

(C) using the illumination angle and the reflective scattering angle associated with the linear photometric data and the refractive index of the medium to calculate corresponding effect flake angles;

(D) fitting the linear photometric data and the effect flake angles with an equation describing the linear photometric data as a continuous function of effect flake angle via computer implementation;

(E) calculating the corresponding effect flake angle from the illumination angle, reflective scattering angle and refractive index of the solid medium for each combination of illumination and reflective scattering angle needed to calculate the BRDF being generated in step (F); and (F) generating the BRDF for each combination of illumination and reflective scattering angle by calculating each value of the BRDF from the corresponding effect flake angle from step (E) above and the equation developed in step (D) above.

Also, the invention is directed to a system for generating BRDF of the gonioapparent material wherein the system comprises a computing device utilizing a computer readable program which causes an operator to perform the above steps (A) through (F).

BRIEF DESCRIPTION OF THE DRAWINGS

For a more complete understanding of the present invention and for further understanding of the advantages thereof, reference is now made to the following detailed description taken in conjunction with the following accompanying drawings.

$$\rho'_{\theta_f} = A \times \exp\left(-\frac{\theta_f}{B}\right) + C \qquad \text{Equation (1)}$$

Figure 8:
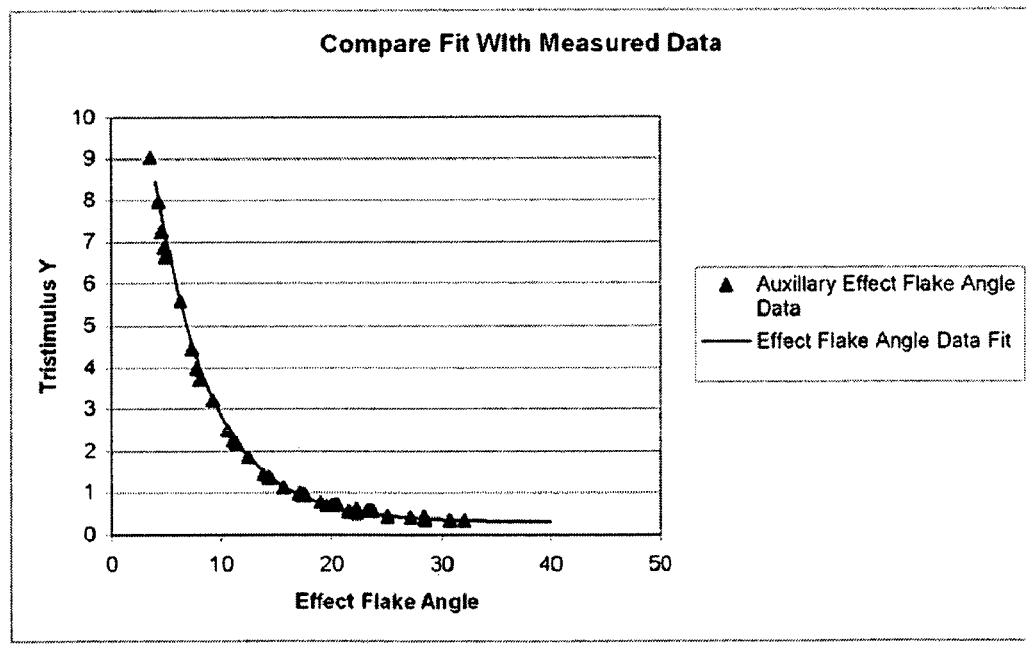

FIG. 8 shows how the curve fit compares with the rest of the measured data that was not used in the calculation of the curve fit.

Figure 9:
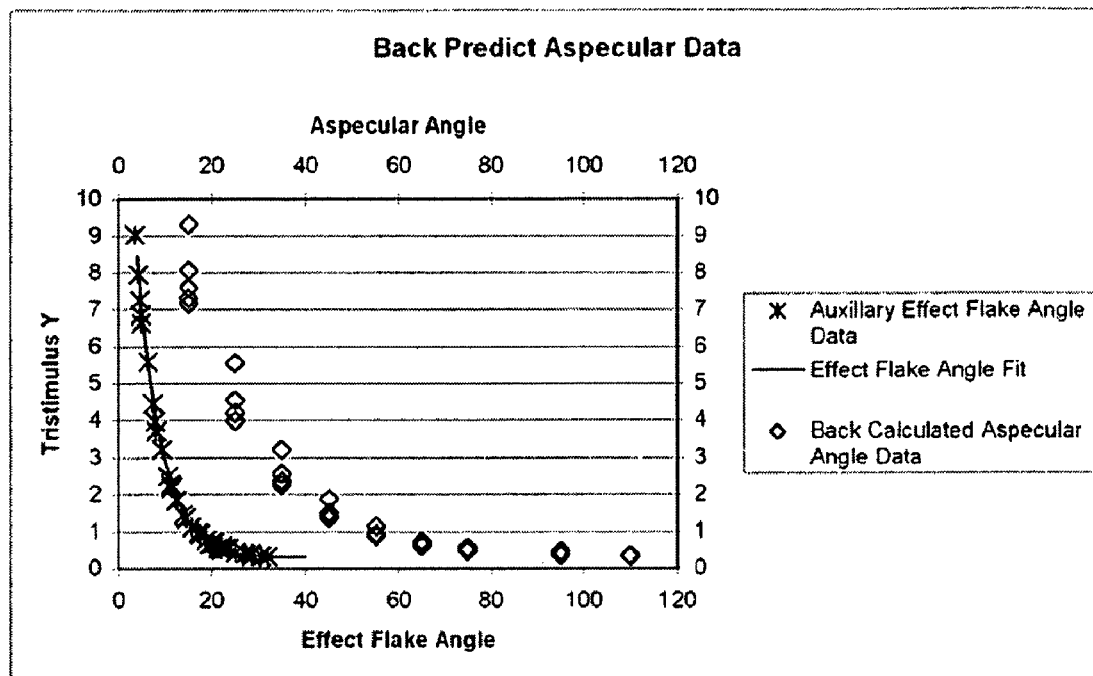

FIG. 9 shows prediction of the measured data from back calculation of the curve fit.

Figure 10:
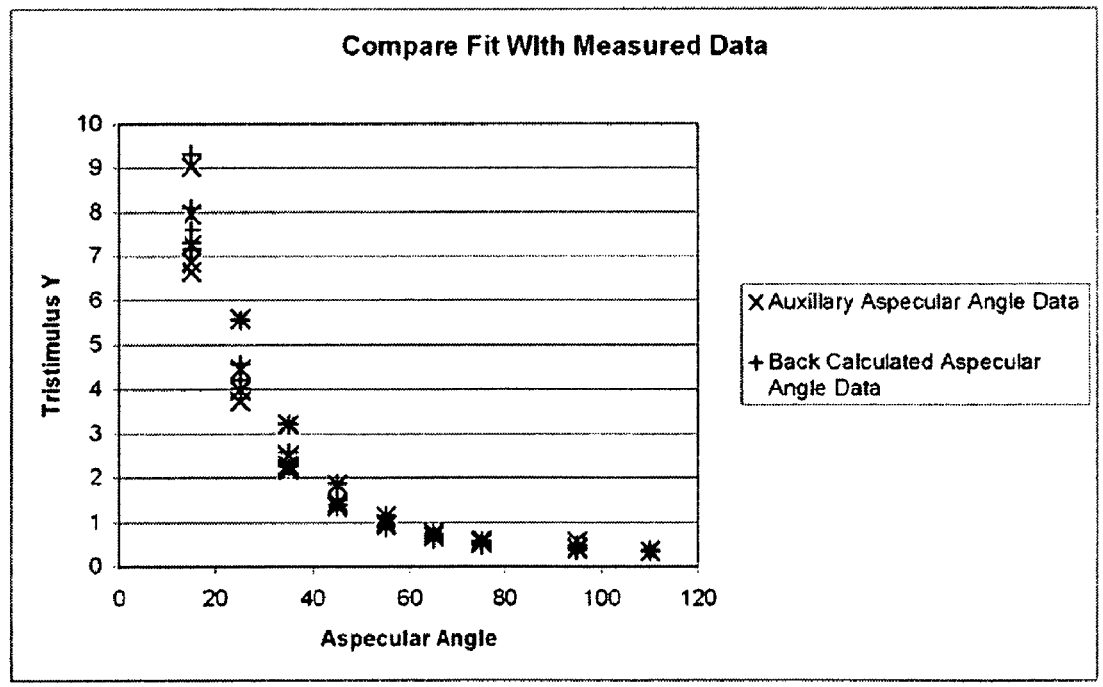

FIG. 10 shows a comparison of the measured and fit data.

Figure 11:
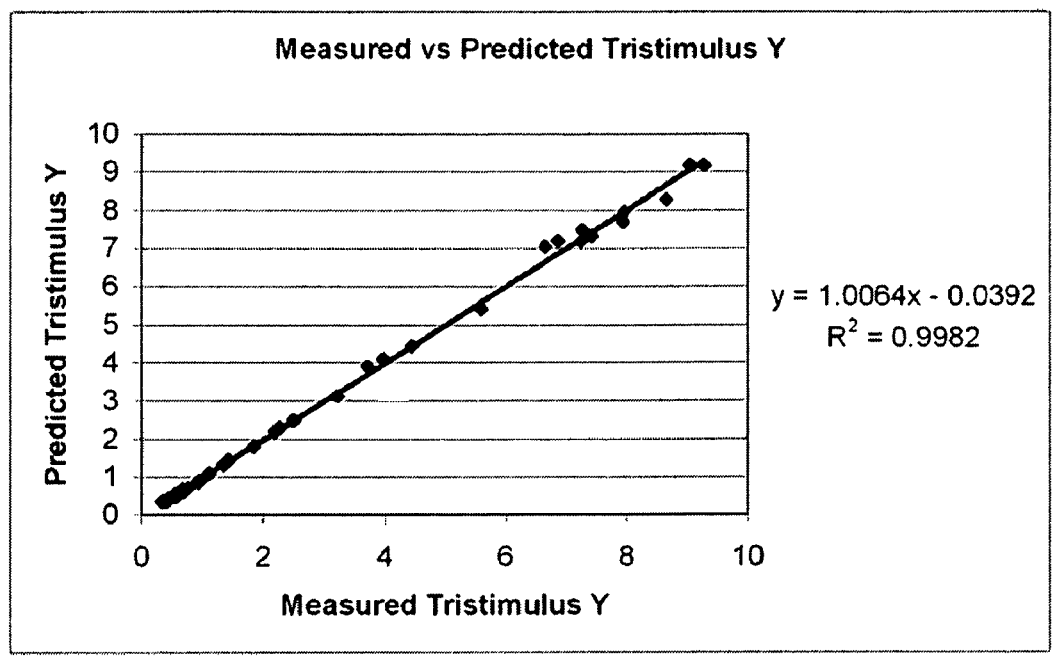

FIG. 11 shows a comparison of the measured and fit data, along with a linear regression fit to the data.

DETAILED DESCRIPTION OF THE EMBODIMENTS

The features and advantages of the present invention will be more readily understood, by those of ordinary skill in the art, from reading the following detailed description. It is to be appreciated that certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both preceded by the word "about." In this manner, slight variations above and below the stated ranges can be used to achieve substantially the same results as values within the ranges. Also, the disclosure of these ranges is intended as a continuous range including every value between the minimum and maximum values.

All patents, patent applications and publications referred to herein are incorporated by reference in their entirety.

The following terms are used herein:

"Effect flake pigments" include metallic flake pigments, such as aluminum flake, coated aluminum flake, gold flake, copper flake, and the like and also includes special effect flake pigments that cause a hue shift, such as, pearlescent pigments, such as, coated mica flake, coated $Al_2O_3$ flake, coated glass flake, coated $SiO_2$ flake, and the like.

"Aspecular angle" the viewing angle measured from the specular direction, in the illuminator plane unless otherwise specified. Positive values of aspecular angle are in the direction toward the illuminator axis.

"Effect flake angle" the angle between the surface normal of the effect flake pigment and the surface normal of the sample specimen.

"Gonioapparent"—pertaining to change in appearance with change in illumination or viewing angle.

"Gonioappearance"—the phenomenon in which the appearance of a specimen changes with change in illumination or viewing angle.

ASTM Standard E 2387-05, which is hereby incorporated by reference, describes procedures for determining the amount and angular distribution of reflective optical scatter from a surface, and provides precise definitions of many of the terms used in the description of the present invention. Definitions for terms not found in ASTM Standard E 2387-05 will be found in ASTM terminology Standard E 284, which is hereby incorporated by reference.

BRDF (bidirectional reflectance distribution function) means a collection of photometric data of any material (herein meaning gonioapparent material) that will describe photometric reflective light scattering characteristics of the material as a function of illumination angle and reflective scattering angle. It is one of the most general and well accepted means of describing the spectral and spatial reflective scattering properties of a gonioapparent material and provides a fundamental description of the appearance of a material and many other appearance attributes (such as, gloss, haze, and color) can be represented in terms of integrals of the BRDF over specific geometries and spectral conditions.

Figure 1:
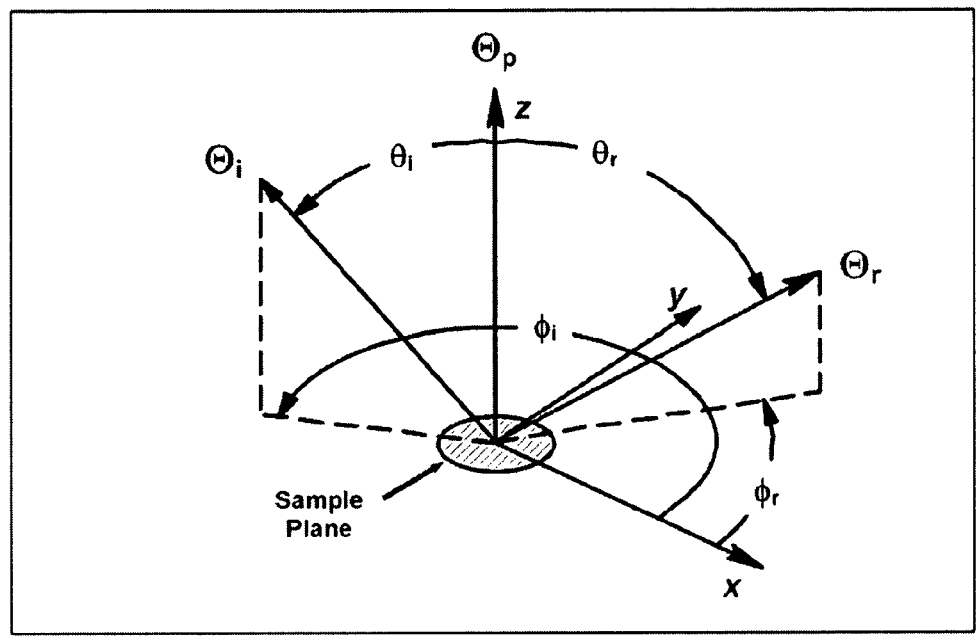
FIG. 1 shows the geometry used in the determination of the BDRF.

The BRDF is dependent on wavelength, incident direction, scatter direction and polarization states of the incident and reflectively scattered fluxes. The BRDF is equivalent to the fraction of incident flux reflectively scattered per unit of projected angle:

$$f_r(\Theta_i, \Theta_s, \lambda) = \frac{dL_{(s)}(\Theta_i, \Theta_s, \lambda)}{dE_{(i)}(\Theta, \lambda)} \quad \text{Equation (2)}$$

Where the subscripts i and r denote incident and reflected respectively, $\Theta=(\theta,\phi)$ is the direction of light propagation, $\lambda$ is the wavelength of light, L is radiance, and E is irradiance. The geometry used by the BRDF is shown in FIG. 1. Where $\Theta_i$ and $\Theta_r$ are the illumination and reflective scattering vectors respectively. $\Theta_p$ is the specimen surface normal vector. $\theta_i$ and $\theta_r$ are the illumination and reflective scattering polar angles respectively, and $\phi_i$ and $\phi_r$ are the illumination and reflective scattering azimuthal angles respectively. "x, y, z" are Cartesian coordinate axes.

In practice, the BRDF of a gonioapparent material is often expressed as directional reflectance factor $R_d$ which is the ratio of the specimen BRDF to that for a perfect reflecting diffuser (defined as $1/\pi$), given by:

$$R_d = \pi f_r \quad \text{Equation (3)}$$

For color work, the BRDF is often expressed as the colorimetric BRDF. The colorimetric BRDF consists of three color coordinates as a function of the scattering geometry. Using CIE color matching functions $[\bar{x}(\lambda), \bar{y}(\lambda), \bar{z}(\lambda)]$ for one of the CIE standard colorimetric standard observers and a CIE standard illuminant $S(\lambda)$, the colorimetric BRDF is defined as:

$$f_{r(color,X)} = k \int_\lambda f_r(\lambda) S(\lambda) \bar{x} d(\lambda) \quad \text{Equation (4)}$$

$$f_{r(color,Y)} = k \int_\lambda f_r(\lambda) S(\lambda) \bar{y} d(\lambda) \quad \text{Equation (5)}$$

$$f_{r(color,Z)} = k \int_\lambda f_r(\lambda) S(\lambda) \bar{z} d(\lambda) \quad \text{Equation (6)}$$

The normalizing factor k is defined as:

$$k = (\int_\lambda S(\lambda) \bar{y}(\lambda) d\lambda) \quad \text{Equation (7)}$$

The specific illuminant (for example, CIE Standard Illuminant D65), set of color matching functions (for example, CIE 1964 Standard Observer) and the color system (for example, CIELAB) must be specified and included with any data.

For purposes of this patent, the term BRDF, as designated by the symbol $f_r$ is meant to include the formal definition of BRDF in terms of reflectance as outlined by, F. E. Nicodemus, J. C. Richmond, J. J. Hsia, I. W. Ginsberg, and T. Limperis, "*Geometrical considerations and nomenclature for reflectance*," NBS Monograph 160 (National Bureau of Standards, Washington, D.C., 1977) as well as any of the normalized variants of the BRDF based on reflectance factor. These variants include, but are not limited to, directional reflectance factor $f_{r(R_2,\lambda)}$, or any of the colorimetric BRDF variants, linear (e.g. $f_{r(color,X)}$, $f_{r(color,Y)}$, $f_{r(color,Z)}$) or non-linear (e.g. $f_{r(colorL)}$, $f_{r(colorM)}$, $f_{r(colorN)}$), including BRDFs generated in RGB space (e.g. $f_{r(RGB,R)}$, $f_{r(RGB,G)}$, $f_{r(RGB,B)}$) often used in the graphic rendering applications. The basic steps of the process of the present invention are the same for all of the BRDF variants with the differences existing in pre-, or post-processing of the data, to convert from one color space to another, known to one skilled in the art.

Changes in the intensity of reflectively scattered light from a material containing effect flake pigments with change in illumination angle or viewing angle are due to the angular distribution of the effect flake pigments in the finish. Typically in a painting process, during drying of paint film applied to a substrate, the effect flake pigments suspended in the paint binder tend to orient themselves roughly parallel to the surface of the substrate being coated. These pigments act as tiny mirrors to specularly reflect light that strikes the pigments. The higher the percentage of effect flake pigment flakes that are oriented so as to act as specular reflectors for a given geometry, the higher the reflected intensity. Other means of specimen preparation of materials containing effect flake pigments will also orient the effect flake pigment flakes to some extent, depending on the method of specimen preparation, e.g., injection molding, or casting.

Figure 2:
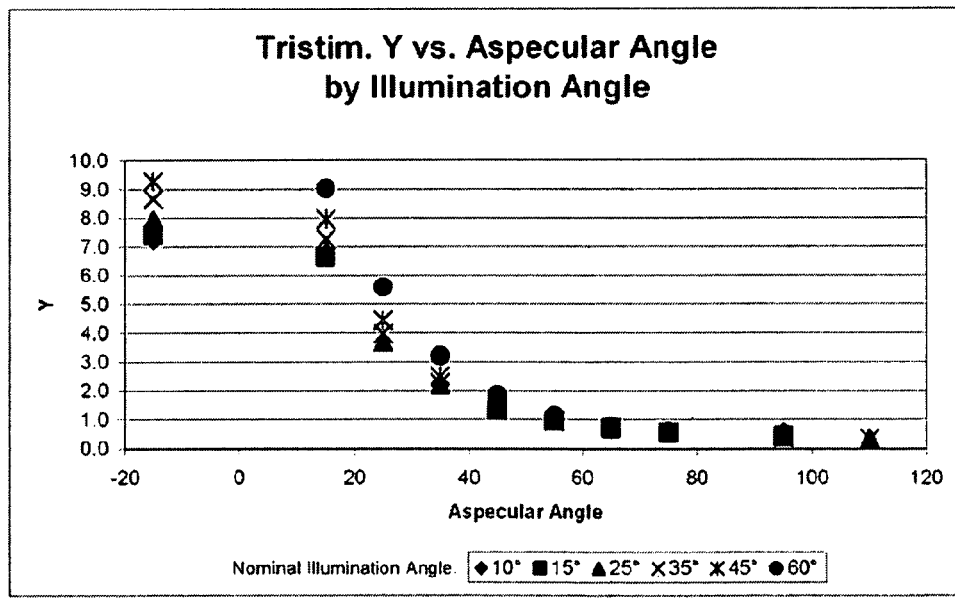
FIG. 2 shows a plot of tristimulus value Y as a function aspecular angle for a number of illumination angles for an automotive paint specimen containing metal flake pigment.

The primary reason for the differences in reflected intensity at a given aspecular angle as a function of illumination angle, as shown in FIG. 2, is that the aspecular geometry is calculated with respect to the surface normal of the material. However due to refraction effects in the paint film, this does not directly describe the angular distribution of the effect flake pigments in the paint film. If the effect flake pigments were suspended in a medium with a refractive index of (1.0) then angle of illumination would not matter; however, this is not the case, and a means to correct for film refraction effects is needed.

Figure 4:
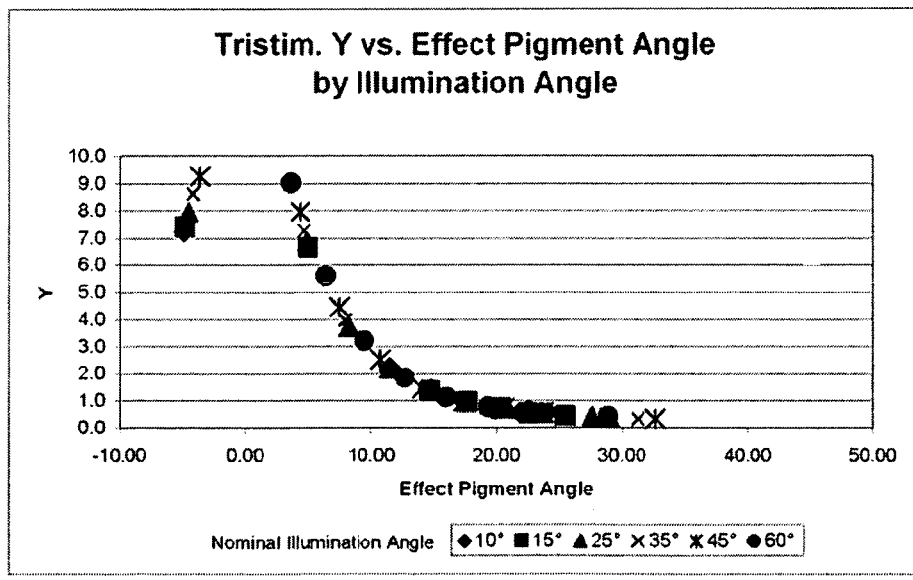
FIG. 4 shows how, through the use of the algorithms embodied in the present invention, the illumination angle dependence of the data shown in FIG. 2 can be eliminated.

Through the use of a process to correct for refraction of the light as it enters and exits the specimen surface, the illumination angle dependence of data in FIG. 2 can be eliminated as shown in FIG. 4.

The following is a step-by-step description of the process used to remove the illumination angle dependence of the data apparent in FIG. 2, and subsequent generation of the BRDF from the processed data. In this description, it is assumed that the specimen plane lies in the x-y plane of a Cartesian coordinate system.

In the first step (A) of the process to generate the BRDF of the specimen, photometric data, $\rho'(\Theta_i, \Theta_r)$, comprising either spectral or colorimetric data as a function of the illumination angle $\Theta_i$, and reflective scattering angle $\Theta_r$, are acquired and input into a computing device. This data may be acquired from a database wherein this photometric data has been previously measured, typically at three different angles, or by actual measurements taken of the specimen, typically at three different angles, or as simulated data for a specimen, typically at three different angles. The combinations of illumination angle and reflective scattering angle typically used are 45:−30(as 15), 45:0(as 45) and 45:65(as 110) resulting in aspecular angles of 15, 45 and 110 degrees. Other appropriate combinations of illumination angle and reflective scattering angle resulting in similar aspecular angle combinations may also be used, such as those resulting in aspecular angle combinations of 15, 45, and 75 degrees and 25, 45 and 75 degrees.

The photometric measurements can be acquired by instruments, such as, the Model GCMS Goniospectrophotometric Measurement System available from Murakami Color Research Laboratory, Tokyo, Japan, or the Model MultiFX10 spectrophotometer available from Datacolor International Incorporated, Lawrenceville, N.J. or the Model MA68 spectrophotometer available from X-Rite Incorporated, Grandville, Mich.

The refractive index of the matrix containing the effect flake pigments, such as a paint, is determined either by measurement with a device, such as, the Model 2010 Prism Coupler available from Metricon Corp., Pennington N.J. or by retrieval from a database.

In step (B) of the process, any non-linear photometric data from step (A) of the process must be converted to a linear photometric basis. For example, any photometric data expressed as CIELAB color coordinates, also commonly referred to as L*a*b* or Lab, must be converted to linear X, Y, Z tristimulus space. L*, a* b* color values are well known to those skilled in the art and represent coordinates in visual uniform color space and are related to X, Y and Z tristimulus values by the following equations which have been specified by the International Committee on Illumination:

$L^*$ defines the lightness axis (Equation 8)

$$L^* = 116\left[f\left(\frac{Y}{Y_0}\right) - \frac{16}{116}\right]$$

$a^*$ defines the red green axis (Equation 9)

$$a^* = 500\left[f\left(\frac{X}{X_0}\right) - f\left(\frac{Y}{Y_0}\right)\right]$$

$b^*$ defines the yellow blue axis (Equation 10)

$$b^* = 200\left[f\left(\frac{Y}{Y_0}\right) - f\left(\frac{Z}{Z_0}\right)\right]$$

where $X_o$, $Y_o$ and $Z_o$ are the tristimulus values of the perfect white for a given illuminant.

and where $f(Y/Y_0) = (Y/Y_0)^{1/3}$ for $Y/Y_0$ greater than 0.008856 and $f(Y/Y_0) = 7.787(Y/Y_0) + 16/116$ for $Y/Y_0$ less than or equal to 0.008856; $f(X/X_0)$ and $f(Z/Z_0)$ are similarly defined.

In step (B) of the process using the above equations, the L* a* b* values for each of the angle combinations utilized are converted into tristimulus X, Y, and Z values as outlined in the following section of computer pseudo-code.

```
If L* < 7.99962
    Then YYN = L*/903.3                        Equation (11)
    Else YYN = ((L* + 16)/116)^3               Equation (12)
End If
Y = YYN × Y_o                                  Equation (13)
If YYN > 0.008856
    Then FYYN = YYN^(1/3)                      Equation (14)
    Else FYYN = 7.787 × YYN + 0.13793          Equation (15)
End If
FXXN = a* / 500 + FYYN                         Equation (16)
If FXXN > 0.206893
    Then XXN = FXXN^3                          Equation (17)
    Else XXN = (FXXN − 0.13793) / 7.787        Equation (18)
End If
X = XXN * X_0                                  Equation (19)
FZZN = FYYN − b*/200                           Equation (20)
If FZZN > 0.206893
    Then ZZN = FZZN^3                          Equation (21)
    Else ZZN = (FZZN − 0.13793) / 7.787        Equation (22)
End IF
Z = ZZN * Z_0                                  Equation (23)
``` where $X_o$, $Y_o$ and $Z_o$ are the above described tristimulus values, and where YYN, FYYN, XXN, FXXN, ZZN, FZZN are intermediate variables used only during the calculation The above equations are shown in ASTM Standard E 308, which is hereby incorporated by reference.

In step (C) of the process the illumination angle dependence of the data is eliminated by converting the data from an aspecular angle basis to an effect flake angle basis. To accomplish this, calculate the unit direction vectors i, r and p for the illumination ray, $\Theta_i = (\theta_i, \phi_i)$, reflectively scattered ray, $\Theta_r = (\theta_r, \phi_r)$, and specimen normal $\Theta_p$ respectively.

$i = (\alpha_i, \beta_i, \gamma_i)$ (Equation 24)

$r = (\alpha_r, \beta_r, \gamma_r)$ (Equation 25)

$p = (\alpha_p, \beta_p, \gamma_p)$ (Equation 26)

where $\alpha^2 + \beta^2 + \gamma^2 = 1$ (Equation 27)

for each of geometries represented in the data acquired in step (A).

The direction cosines $\alpha$, $\beta$, $\gamma$ are determined from the polar and azimuthal angles $\theta$ and $\phi$ as follows:

$\alpha = \sin\theta \cos\phi$ (Equation 28)

$\beta = \sin\theta \sin\phi$ (Equation 29)

$\gamma = \cos\theta$ (Equation 30)

Next, calculate the cosine of the included angle $\tau_{ip}$ between the incident ray direction vector i and the specimen surface normal p.

$\cos\tau_{ip} = \alpha_i^* \alpha_p + \beta_i^* \beta_p + \gamma_i^* \gamma_p$ (Equation 31)

Similarly, also calculate the cosine of the included angle $\tau_{rp}$ between the reflectively scattered ray direction vector r and the specimen surface normal direction vector p, $\cos\tau_{rp} = \alpha_r^* \alpha_p + \beta_r^* \beta_p + \gamma_r^* \gamma_p$ (Equation 32)

Figure 3:
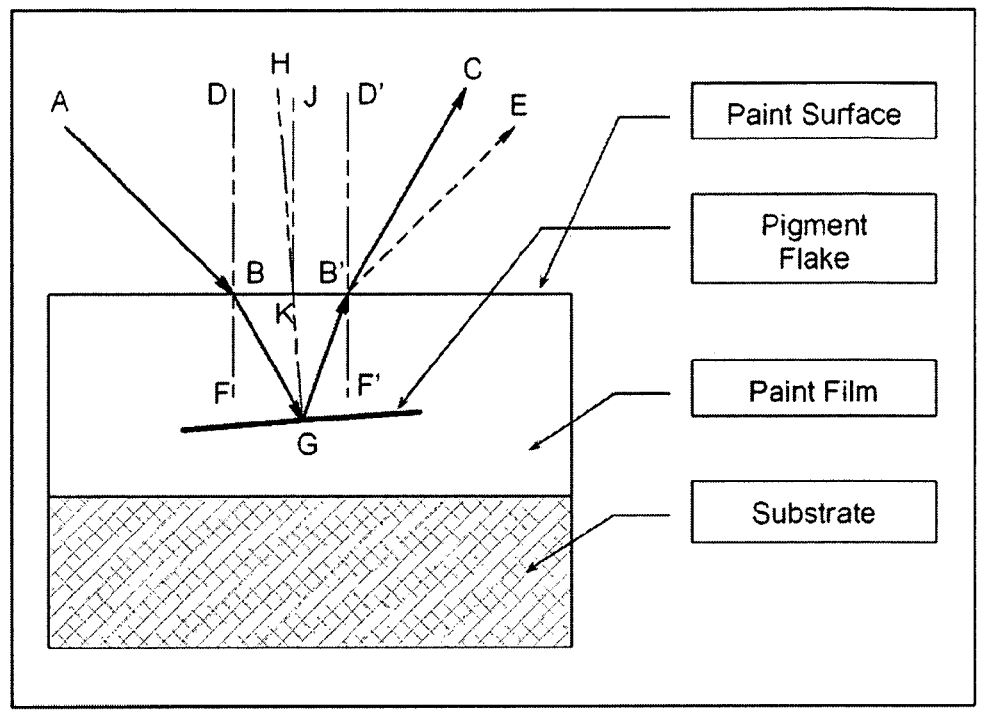
FIG. 3 shows a schematic of how a ray of light is specularly reflected from a metal flake suspended in a paint film.

The angles $\tau_{ip}$ and $\tau_{rp}$ are shown in two dimensions in FIG. 3 as angles $\angle ABD$ and $\angle CB'D'$ respectively.

As illustrated in two dimensions in FIG. 3, as the incident ray $\overline{AB}$ passes through the surface of the specimen matrix, it is refracted toward the surface normal $\overline{BF}$, as ray $\overline{BG}$. Similarly the reflectively scattered ray $\overline{GB'}$ is refracted away from the surface normal $\overline{B'D'}$ as it passes out of the specimen matrix as ray $\overline{B'C}$. Rays $\overline{BG}$ and $\overline{GB'}$ represent the in-matrix illumination ray $\Theta_{i'}$ and the in-matrix reflectively scattered ray $\Theta_{r'}$ respectively. Next determine the direction vector i' of in-matrix illumination ray $\Theta_{i'}$ and the direction vector s' of in-matrix reflective scattered ray $\Theta_{r'}$ from angles $\angle ABD$, $\tau_{ip}$ above, and $\angle CB'D'$, $\tau_{rp}$ above in conjunction with the refractive index of the specimen matrix $\eta_2$ and the refractive index of air $\eta_1$ using the vector form of Snell's law:

$$\cos\tau_{i'p} = \sqrt{1 - \left(\frac{\eta_1}{\eta_2}\right)^2 (1 - (\cos\tau_{ip})^2)} \quad \text{(Equations 33 \& 34)}$$

$$i'_{\alpha,\beta,\gamma} = \left(\frac{\eta_1}{\eta_2}\right) i_{\alpha,\beta,\gamma} + \left(\cos\tau_{i'p} - \frac{\eta_1}{\eta_2}\cos\tau_{ip}\right) p_{\alpha,\beta,\gamma}$$

and $$\cos\tau_{r'p} = \sqrt{1 - \left(\frac{\eta_1}{\eta_2}\right)^2 (1 - (\cos\tau_{rp})^2)} \quad \text{(Equations 35 \& 36)}$$

$$r'_{\alpha,\beta,\gamma} = \left(\frac{\eta_1}{\eta_2}\right) r_{\alpha,\beta,\gamma} + \left(\cos\tau_{r'p} - \frac{\eta_1}{\eta_2}\cos\tau_{rp}\right) p_{\alpha,\beta,\gamma}$$

For a effect flake pigment flake to act as a specular reflector for a particular geometry, its surface normal must bisect the angle formed by the in-matrix illumination ray and the in-matrix reflective scattering ray. The surface normal vector of the effect flake pigment flake is calculated as follows:

$$\Theta_f = i'_{\alpha,\beta,\gamma} + r'_{\alpha,\beta,\gamma} \quad \text{(Equation 37)}$$

converting $\Theta_f$ from its Cartesian form $\Theta_f = (\alpha_f \beta_f \gamma_f)$ to its spherical coordinate form $\Theta_f = (\theta_f, \phi_f)$, the polar angle $\theta_f$ describes the angle of the effect flake pigment flake surface normal to the specimen surface normal which we call the effect flake angle.

In step (D) of the process, the linear photometric data, $\rho'$, from step (B) and the effect flake angle data, $\theta_f$, from step (C) are fit via computer implementation with an equation which describes the photometric data as a continuous function of the effect flake angle. A useful functional form for this equation is the exponential decay plus constant equation of the form:

$$\rho'_{\theta_f} = A \times \exp\left(-\frac{\theta_f}{B}\right) + C \quad \text{(Equation 1)}$$

Where A, B, C are weighting constants calculated in the curve fitting process.

While the exponential decay function is well suited to fit typical data, there are equations of other functional forms which may also be useful.

In step (E) of the process, for each geometry to be calculated in the BRDF, the effect flake angle, $\theta_f$, for the geometry is calculated using the same procedure as described in step (C) of the process substituting the BRDF geometry for the measurement geometry.

In step (F) of the process, for each geometry to be calculated in the BRDF, the value of the BRDF is calculated by solving the equation:

$$f_{r(\theta_i,\phi_i,\theta_r,\phi_r)} = A \times \exp\left(-\frac{\theta_{f(\theta_i,\phi_i,\theta_r,\phi_r,\eta_2)}}{B}\right) + C \quad \text{(Equation 38)}$$

using the value of $\theta_{f(\theta_1,\phi_1,\theta_1,\phi_1,\eta_2)}$ from step (E) of the process and weighting coefficients A, B, C from step (D) of the process.

In an optional step (G) the linear BRDF values calculated in steps (A-F) can be converted to non-linear BRDF values as necessary, e.g. if the desired final BRDFs are in non-linear L*a*b* space they must be calculated from linear BRDFs in XYZ space. The mathematics of this conversion are known to those skilled in the art.

Once the BRDF has been generated, the data contained in the BRDF can be used for a wide variety of purposes. One of the most widely used uses of BRDF data is for rendering the appearance of an object on some display media such as a video display device, print media, photographic media and the like. The processes and computational algorithms for generating display R,G,B values based on BRDF, integrating the display R,G,B values with shapes of the object, and rendering appearance of the object are well known to those skilled in the art. There are also a variety of commercial and proprietary computer programs available to do the object rendering including U-Drive from Bunkspeed of Los Angeles, Calif., Opus Realizer from Opticore AB of Gothenburg, Sweden, Maya from Autodesk of San Rafael, Calif., and the like.

An example of a process for rendering appearance of an object based on BRDF can be described briefly below. A user first selects color to be rendered for the object. Color data corresponding to the selected color is retrieved from a color database or acquired by measuring the object using methods well known to those skilled in the art. The process is described in detail by Rupieper et al. (U.S. Pat. No. 6,618,050) and Voye et al. (U.S. Pat. No. 6,977,650). Line 62 of column 4 through line 44 of column 8 of the aforementioned U.S. Pat. No. 6,618,050, and line 5 of column 6 through line 45 of column 11 of the aforementioned U.S. Pat. No. 6,977,650 are incorporated herein by reference. In brief, images or surface topographies of the object are facetted into a sufficient number of polygons to generate polygon data. One or more illumination and viewing angles can be selected or simulated to generate illumination and viewing angle data. The polygon data, the illumination and viewing angle data, and BRDF data based on this invention are integrated into a computing process to convert X,Y,Z BRDF color data of the selected color into display X,Y,Z data that reflect appearance of the selected color under said illumination and viewing angles. The display X,Y,Z data can be scaled up or down as determined necessary by those skilled in the art. Display R,G,B data can be defined based on the display X,Y,Z data. Depending on the display devices, the display R,G,B data may need to be calibrated or adjusted based on the display device profile. The process is repeated for each of plurality of pixels of the polygon and each of the illumination and viewing angles, and each of the sufficient number of polygons. The appearance of the object is then displayed via the display device.

In addition to its use in rendering applications, the data contained in the BDRF generated by the present invention can be used for a variety of other uses. The absolute color or reflectance data can be used in conjunction with pigment mixture models to aid in the formulation of paint finishes or molded plastic products containing effect flake pigments, to assess and insure color match at a wide variety of illumination and viewing conditions. BDRF data can be used to predict the visual differences between surfaces, coated with the same or different materials, presented to the observer at slightly different geometries, e.g., the BRDF data can be used to assess color match between an automobile body and body fascia such as bumper covers or other trim. Color difference data calculated from the BRDF data of two or more specimens can be used for a variety of different color shading and control applications. While the example uses of BRDF data cited above represent typical uses of this data it is not meant to be a restrictive or complete list of uses for the BRDF data.

EXAMPLE

The present invention is further defined in the following Example. It should be understood that this Example, while indicating preferred embodiments of the invention, is given by way of illustration only. From the above discussion and this Example, one skilled in the art can ascertain the essential characteristics of this invention, and without departing from the spirit and scope thereof, can make various changes and modifications of the invention to adapt it to various uses and conditions.

Example 1

The following example demonstrates and illustrates the steps required to generate an L* colorimetric BRDF for an automotive paint sample containing metal flake effect flake pigments. The L* colorimetric axis is used as an example only, and the same basic steps are required for calculation of other colorimetric BRDF axes or directional reflectance factor.

In step (A) of the process, the sample specimen is placed in a Model GCMS Goniospectrophotometric Measurement System which has been calibrated according to the manufacture's established procedure. L*a*b* measurements of the specimen are made at the following set of illumination and viewing geometries:

$\theta_{i1}$=45 degrees, $\phi_{i1}$=0 degrees, $\theta_{s1}$=30 degrees, $\phi_{s1}$=180 degrees      1)

$\theta_{i2}$=45 degrees, $\phi_{i2}$=0 degrees, $\theta_{s2}$=0 degrees, $\phi_{s2}$=0 degrees      2)

$\theta_{i3}$=45 degrees, $\phi_{i3}$=0 degrees, $\theta_{s3}$=75 degrees, $\phi_{s3}$=0 degrees      3)

These geometries represent measurements at aspecular angles of 15 degrees, 45 degrees, and 110 degrees respectively. The L*a*b* measurements acquired are as follows:

$L^*_1$=33.90, $a^*_1$=−7.58, $b^*_1$=−36.61      1)

$L^*_2$=12.29, $a^*_2$=1.19 $b^*_2$=−25.77      2)

$L^*_3$=3.07, $a^*_3$=2.09 $b^*_3$=−13.24      3)

Additionally the refractive index of the paint matrix is measured on a Metricon Model 2010 Prism Coupler which has been set-up and calibrated according to the manufacture's established recommended procedure. The refractive index of the specimen matrix $\eta_2$ is measured to be 1.5109.

In addition to the data above, L*a*b* measurements were also made at a variety of other measurement geometries which although not required for the present invention will be used later in this example to demonstrate the utility of the present invention.

In step (B) of the process, look at the photometric data acquired in step (A) and find that the data is non-linear L*a*b* data and therefore must be converted to a linear basis, in this case conversion to tristimulus X,Y,Z space is appropriate. Using equations (11-23) the L*,a*,b* data is converted to X,Y,Z data. Since this example only demonstrates generation of an L* colorimetric BRDF only the Y values are calculated as the L* value has no X, or Z component. The Y values associated with the three acquired measurements above are as follows:

$Y_1$=7.96      1)

$Y_2$=1.45      2)

$Y_3$=0.34      3)

Figure 5:
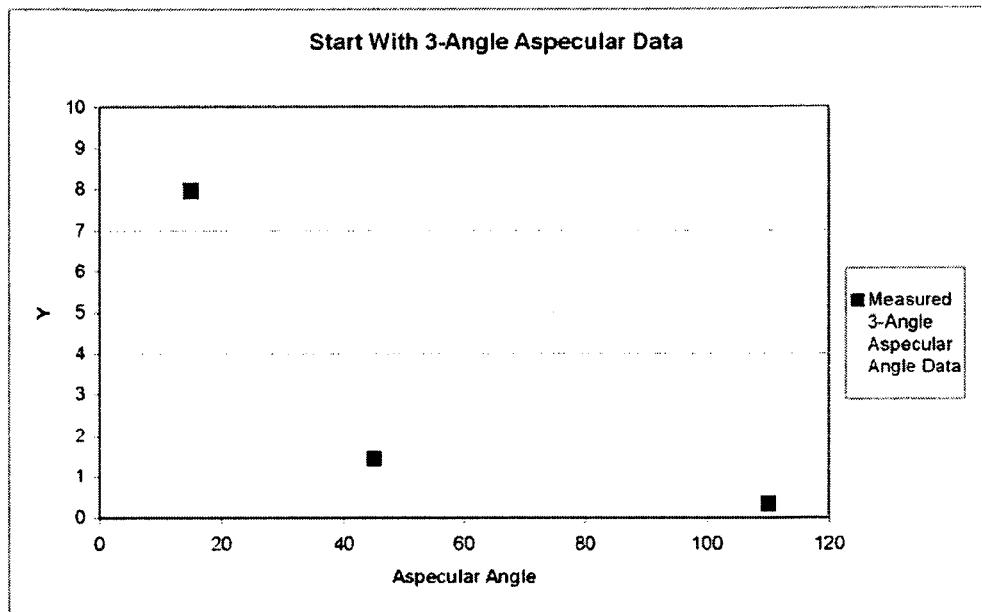
FIG. 5 shows the three measurements used in step (B) of the example demonstration of the present invention.

FIG. 5 shows a plot of this Y data versus aspecular angle.

Using the equations outlined in step (C) of the process description, the measurement geometries associated with the photometric data are converted to an effect flake angle basis. The effect flake angles associated with each of the measurements are as follows:

$\theta_{f1}$=4.25 degrees      1)

$\theta_{f2}$=13.82 degrees      2)

$\theta_{f3}$=32.07 degrees      3)

Figure 6:
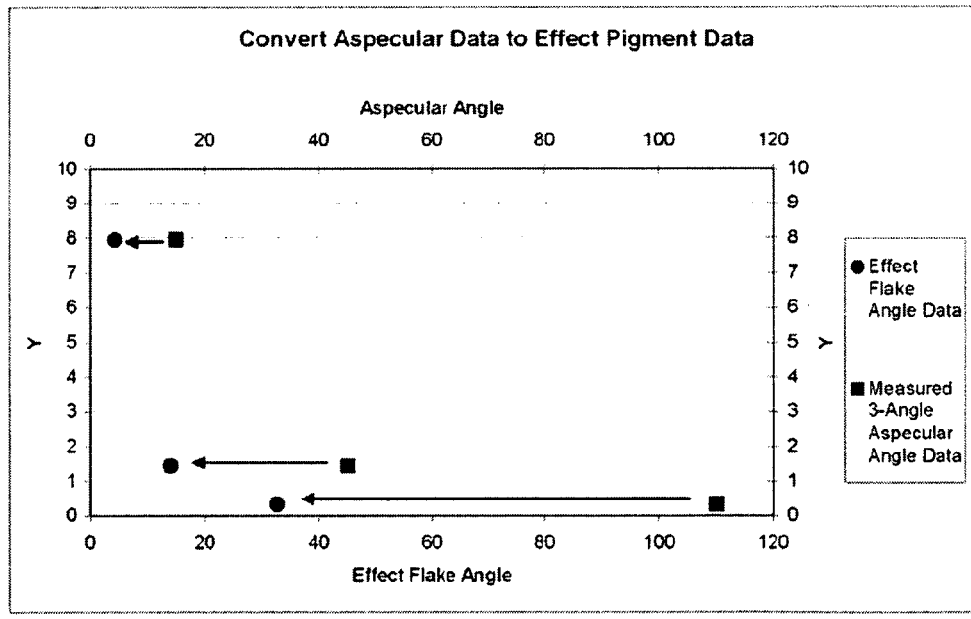
FIG. 6 shows the conversion of the data in FIG. 5 from being a function of aspecular angle to being a function of effect flake angle.

FIG. 6 shows a plot of the conversion on the Y data from an aspecular angle basis (square symbols) to an effect flake angle basis (circular symbols).

In step (D) of the process the photometric p data (Y data in this example) from step (B) of the process, and the effect flake angle data, $\theta_f$, from step (C) of the process are fit via computer implementation with an equation of the form:

$$\rho'_{\theta_f} = A \times \exp\left(-\frac{\theta_f}{B}\right) + C \qquad \text{(Equation 1)}$$

The coefficients of the equation, A, B, C are as follows:

A=17.86, B=1.45, C=0.34

Figure 7:
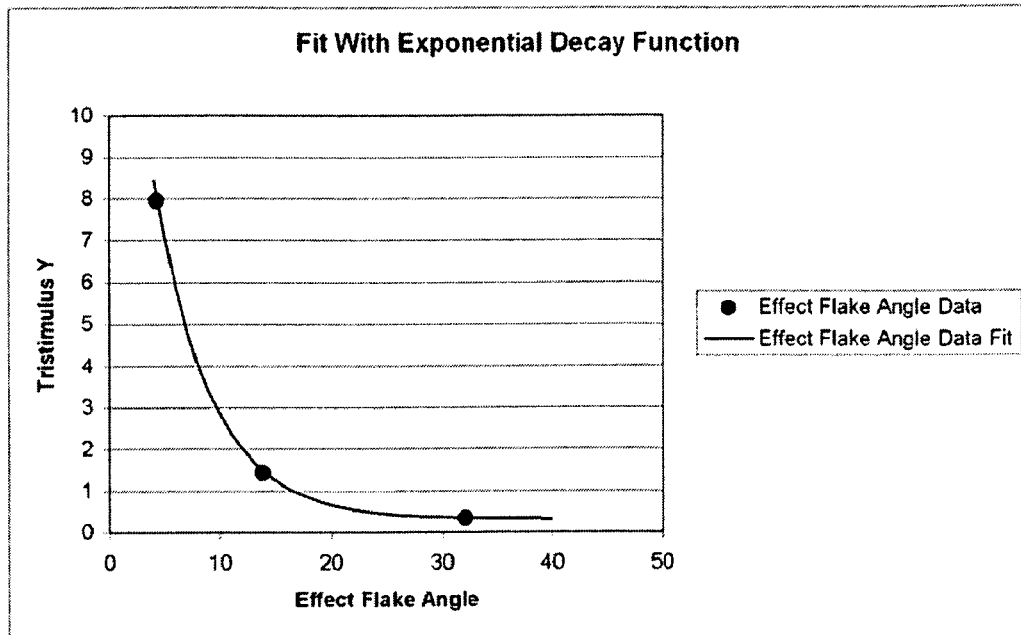
FIG. 7 shows the fit of the example effect flake angle data with an equation of the form.

FIG. 7 shows a graph of the function above plotted with the coefficients above as a function of effect flake angle. Note that the experimental data points (circular symbols) are fit exactly.

In step (E) of the process, for each geometry to be calculated in the BRDF, the effect flake angle for the geometry is calculated using the same procedure as described in step (C) of the process substituting the BRDF geometry for the measurement geometry. For purposes of this example, use the measurement geometries associated with the extra measurements made in step (A) of the example above as the BRDF geometries to be modeled.

FIG. 8 shows a plot of the extra measurements acquired in step (A) above after conversion to effect flake angle basis superimposed on top of the curve fit through the original data. Note the excellent agreement between the predicted data (solid curve) and the measured data (diamond shaped symbols). Since the measured data represents measurements taken at a wide variety of illumination angles, this demonstrates that the process outlined in this invention is capable of removing the illumination angle dependence of the data as shown in FIG. (2). FIG. (9) shows the BRFD predicted data plotted once again as a function of aspecular angle. FIG. (10) shows a comparison of the measured and fit data plotted versus aspecular angle. FIG. (11) shows a plot of measured versus predicted data along with linear regression fit of the data. The slope of the regression fit being close to a value of 1.0, the value of the intercept being close to a value of 0.0, along with the goodness-of-fit statistic $R^2$ value being close to 1.0 indicate that the model and hence, the procedure as outlined here is useful predicting the BRDF of a specimen containing effect pigments with a very limited (in this case 3 measurement points) amount of data. As is to be expected, the largest deviations in predicted data vs. measured data occur where the slope of the fitted curve is steep, the small deviations shown here are not expected to be visually objectionable in a rendering produced using this technique.

This same procedure has also be shown to work well with finishes containing most hue shifting pigments, such as coated mica flakes, and the like.

What is claimed is:

1. A computer-implemented process for producing a predicted visual display of an object coated with a gonioapparent material containing effect flake pigments in a solid medium, said process comprising the steps of:
   (i) generating a bidirectional reflectance distribution function (BRDF) of said gonioapparent material using limited measurement data, said BRDF is generated by a BRDF process comprising the following steps in any appropriate order:
      (A) acquiring and inputting into a computing device (1) photometric data comprising spectral or colorimetric data of the gonioapparent material being a function of an illumination angle and a reflective scattering angle, wherein said data being obtained by (a) measurements of the gonioapparent material, (b) previously measured data of the gonioapparent material from a data base containing measurements of the gonioapparent material or (c) simulated data for a gonioapparent material and (2) the refractive index of the solid medium of the gonioapparent material;
      (B) converting any non-linear photometric data from step (A) above to linear photometric data;
      (C) using the illumination angle and the reflective scattering angle associated with the linear photometric data and the refractive index of the medium to calculate corresponding effect flake angles;
      (D) fitting the linear photometric data and the effect flake angle data with an equation describing the linear photometric data as a continuous function of effect flake angle via computer implementation;
      (E) calculating the corresponding effect flake angle from the illumination angle, reflective scattering angle and refractive index of the solid medium for each combination of illumination and reflective scattering angle needed to calculate the BRDF being generated in step (F) and
      (F) generating the BRDF for each combination of illumination and reflective scattering angle by calculating each value of the BRDF from the corresponding effect flake angle from step (E) above and the equation developed in step (D) above;
   (ii) producing R,G,B values based on said BRDF and shapes of the object, or a portion thereof, and
   (iii) producing said predicted visual display of said object on a display media based on said R,G,B values.

2. The computer-implemented process of claim 1 further comprising the steps of:
   (ia) calculating color difference or spectral reflectance difference data using said BRDF for said object coated with a different material, at a different geometry, or a combination thereof;
   (iia) producing a subsequent visual display based on said shapes of the object, said BRDF and said color difference or spectral reflectance difference data of said object.

3. The computer-implemented process of claim 2, wherein said predicted visual display and said subsequent visual display are displayed on the same or different display media.

4. The computer-implemented process of claim 1, wherein the BRDF generated is used to calculate the absolute colorimetric or spectral reflectance data for the object at angles not specifically measured in step (A).

5. The computer-implemented process of claim 1, wherein three combinations of illumination and reflective scattering angle are used in step (A) and subsequent steps.

6. The computer-implemented process of claim 5, wherein up to ten combinations of illumination and reflective scattering angle are used in step (A) and subsequent steps.

7. The computer-implemented process of claim 5, wherein the three combinations of illumination and reflective scattering angle result in detection at aspecular angles of 15, 45 and 110 degrees.

8. The computer-implemented process of claim 1, wherein the BRDF are combined with spatial texture information to render the predicted visual display of said object.

9. The computer-implemented process of claim 1 wherein the predicted visual display of the object is rendered on a video display device.

10. The computer-implemented process of claim 1, wherein the predicted visual display of the object is rendered on print media.

11. The computer-implemented process of claim 1, wherein the predicted visual display of the object is rendered on photographic media.

12. The computer-implemented process of claim 1, wherein the pigments in the gonioapparent material are aluminum flake pigments.

13. The computer-implemented process of claim 1, wherein the pigments in the gonioapparent material are hue shifting flake pigments.

14. The computer implemented process of claim 1 further comprising an optional step (G) that converts the BRDF to a non-linear basis.

* * * * *